(12) United States Patent
Goldie et al.

(10) Patent No.: US 11,278,289 B2
(45) Date of Patent: *Mar. 22, 2022

(54) TRANSCATHETER DEVICE AND MINIMALLY INVASIVE METHOD FOR CONSTRICTING AND ADJUSTING BLOOD FLOW THROUGH A BLOOD VESSEL

(71) Applicant: Vivonics, Inc., Bedford, MA (US)

(72) Inventors: James H. Goldie, Lexington, MA (US); Brendan LaBrecque, Middleton, MA (US); Anna M Galea, Stow, MA (US); Eric Klem, Lexington, MA (US); Thomas Doyle, Brentwood, TN (US); Ian Cohen, Broomfield, CO (US); Tim Robinson, Sandown, NH (US)

(73) Assignee: Vivonics, Inc., Bedford, MA (US)

( * ) Notice: Subject to any disclaimer, the term of this patent is extended or adjusted under 35 U.S.C. 154(b) by 52 days.

This patent is subject to a terminal disclaimer.

(21) Appl. No.: 16/728,028

(22) Filed: Dec. 27, 2019

(65) Prior Publication Data

US 2020/0146683 A1 May 14, 2020

Related U.S. Application Data

(63) Continuation of application No. 15/420,772, filed on Jan. 31, 2017, now Pat. No. 10,568,634.
(Continued)

(51) Int. Cl.
*A61F 2/82* (2013.01)
*A61B 17/12* (2006.01)
(Continued)

(52) U.S. Cl.
CPC .. *A61B 17/12036* (2013.01); *A61B 17/12109* (2013.01); *A61B 17/12172* (2013.01); *A61B 17/12177* (2013.01); *A61F 2/82* (2013.01); *A61M 29/02* (2013.01); *A61B 2017/12054* (2013.01); *A61F 2002/068* (2013.01)

(58) Field of Classification Search
CPC ........ A61B 17/12109; A61B 17/12036; A61B 17/12177; A61B 17/12172; A61B 2017/12054; A61M 29/02; A61F 2/82; A61F 2002/068
See application file for complete search history.

(56) References Cited

U.S. PATENT DOCUMENTS 5,662,711 A  9/1997  Douglas
6,120,534 A  9/2000  Ruiz
(Continued)

FOREIGN PATENT DOCUMENTS

WO  2015114471 A1  8/2015

OTHER PUBLICATIONS

Written Opinion of th International Searching Authority, dated Apr. 7, 2017 in International Application No. PCT/US2017/015826, five (5) pages (unnumbered).

*Primary Examiner* — Dinah Baria
(74) *Attorney, Agent, or Firm* — Iandiorio Teska & Coleman, LLP

(57) ABSTRACT

A pulmonary artery flow restrictor system includes a funnel shaped membrane with a proximal base and a restrictive distal opening which is stretchable to larger sizes. A self-expanding frame is attached to the proximal base of the membrane for securing the membrane within the pulmonary artery.

16 Claims, 8 Drawing Sheets

Related U.S. Application Data

(60) Provisional application No. 62/289,402, filed on Feb. 1, 2016.

(51) Int. Cl.
*A61M 29/02* (2006.01)
*A61F 2/06* (2013.01)

(56) References Cited

U.S. PATENT DOCUMENTS

| | | |
|---|---|---|
| 6,638,257 B2 | 10/2003 | Amplatz |
| 2007/0060946 A1* | 3/2007 | Keegan ............... A61M 25/104 |
| | | 606/200 |
| 2011/0046611 A1 | 2/2011 | Christiansen |
| 2014/0012181 A1 | 1/2014 | Sugimoto et al. |
| 2014/0046426 A1 | 2/2014 | Kovalsky |
| 2014/0236211 A1 | 8/2014 | Naja |
| 2014/0350667 A1 | 11/2014 | Braido et al. |
| 2014/0371778 A1 | 12/2014 | Rudakov et al. |
| 2015/0142103 A1 | 5/2015 | Vidlund |

* cited by examiner

TRANSCATHETER DEVICE AND MINIMALLY INVASIVE METHOD FOR CONSTRICTING AND ADJUSTING BLOOD FLOW THROUGH A BLOOD VESSEL

RELATED APPLICATIONS

This application is a continuation of U.S. patent application Ser. No. 15/420,772 filed Jan. 31, 2017 and claims benefit of and priority to U.S. Provisional Application Ser. No. 62/289,402 filed Feb. 1, 2016, under 35 U.S.C. § 119, 120, 363, 365, and 37 C.F.R. § 1.55 and § 1.78, which are incorporated herein by this reference.

GOVERNMENT RIGHTS

This invention was made with government support under HHSN268201400058C, awarded by the National institutes of Health. The government has certain rights in the invention.

FIELD OF THE INVENTION

This invention relates to a pulmonary artery restriction device and a minimally invasive method for constricting and adjusting blood flow through a blood vessel.

BACKGROUND OF THE INVENTION

Congenital heart disease (CHD) refers to the various malformations of the heart and surrounding vessels that occur prior to birth. Almost 1% of children are born with some form of significant CHD. CHD remains a leading cause of infant death in the United States. Many infants with CHD develop exuberant blood flow to their lungs that, if left untreated, may result in overwhelming congestive heart failure and death. For example, in ventricular septal defect (VSD), the most common type of CHD occurring in about 37% of cases, holes in the septum allows oxygen rich blood entering into the left ventricle from the lungs to leak out to the right ventricle and escape out the pulmonary artery instead of out the aorta and to the rest of the body. When, however, complete surgical repair in infancy is not possible or not ideal, it becomes imperative that the pulmonary blood flow be restricted in order to allow the infant to thrive to an age where repair is feasible. The current approach for many of these children is to surgically limit their pulmonary blood flow. This can be accomplished by cinching down on the main or branch pulmonary arteries with a band (pulmonary artery band) or by completely removing the natural flow to the lungs and replacing it with a controlled source of blood flow through a Gortex shunt or surgical conduit. See published U.S. Application No. 2014/0236211 and U.S. Pat. No. 5,662,711 both incorporated herein by this reference.

Although effective in controlling pulmonary blood flow, the pulmonary artery band results in distortion of the pulmonary arteries which can negatively impact future surgical intervention. In addition, the pulmonary artery band can only be adjusted through additional surgery. Similarly, placement of a surgical shunt or conduit may result in distortion of the pulmonary arteries. Such artificial connections have the potential for thrombosis, distortion and occlusion, which may have fatal consequences. See also U.S. Pat. No. 6,638,257 and WO 2015/114471 both incorporated herein by this reference.

SUMMARY OF THE INVENTION

Featured is a pulmonary artery flow restrictor system comprising a funnel shaped membrane with a proximal base and a restrictive distal opening which is stretchable to larger sizes and a self-expanding frame attached to the proximal base of the membrane for securing the membrane within the pulmonary artery.

In one example, the frame includes arms extending upward over the membrane distal opening. The funnel shaped membrane may be made of a polymer, for example, polytetrafluoroethylene (ePTFE). The frame may be made of a shape memory alloy, for example, Nitinol.

The frame may include a stent like structure with a series of spaced upper and lower apexes. Preferably, the spaced lower apexes are secured to the proximal base of the membrane. In one example, the frame further includes a plurality of bent anchoring arms extending upwardly over the membrane distal opening each formed from members extending from adjacent frame upper apexes. The arms may cross above the membrane distal opening. The pulmonary artery flow restrictor may further include one or more flexible lines connected to the frame for collapsing the frame.

The pulmonary artery flow restrictor system may further include a transcatheter device for delivering the membrane and frame into the pulmonary artery. In one example, the transcatheter device includes an inner lumen about a guide wire and a retractable lumen retractable relative to the inner lumen. The frame may be removably attached to the inner lumen, using, for example, pins attached to the inner lumen and frame eyelets receiving said pins therethrough.

Also featured is a pulmonary artery flow restrictor comprising a membrane including a restrictive opening. The membrane is made of a material which is irreversibly stretchable to larger sizes by a balloon catheter to vary the size of the restrictive opening. A self-expanding frame is attached to the membrane for securing the membrane within the pulmonary artery. Preferably the frame includes arms extending upward over the membrane restrictive opening. The membrane is preferably made of a polymer such as polytetrafluoroethylene (ePTFE).

The development of a percutaneous intravascular pulmonary artery resistor would avoid the complications associated with these conventional techniques and have the potential for non-surgical adjustment over time to accommodate for growth. Such a device would greatly impact the treatment approach to many children with congenital heart disease. In addition, it would provide a minimally invasive approach for palliation of children in parts of the world where access to surgery is limited or nonexistent. Such an approach ultimately relies on surgery for definitive treatment in these children, but it replaces a series of operations with a single operation that can be planned and scheduled well in advance.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
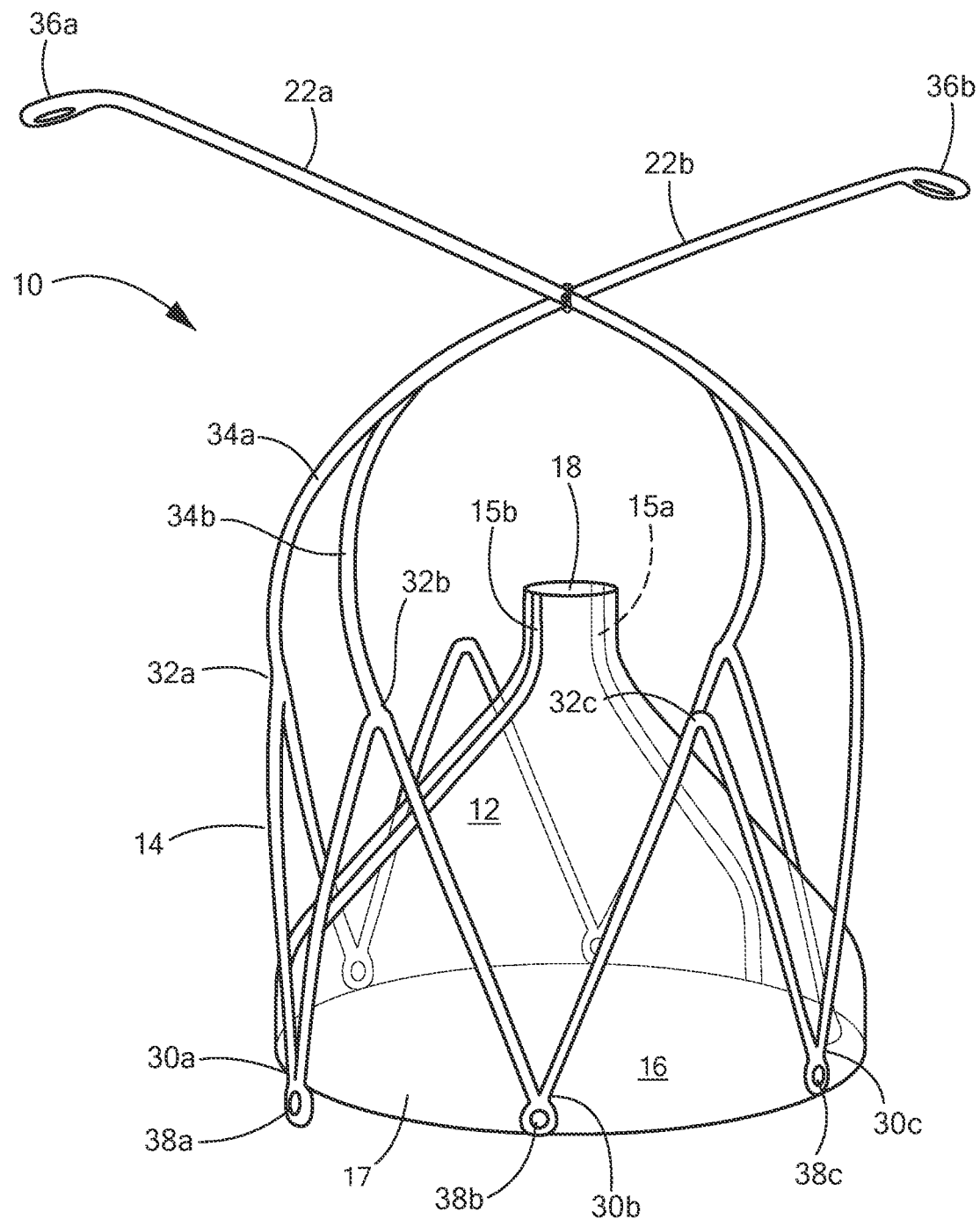
FIG. 1 a schematic view showing an example of a pulmonary artery flow resistor in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

One or more embodiments of the transcatheter device and minimally invasive method for constricting and adjusting blood flow through a blood vessel of this invention provides a minimally invasive surgery (MIS) device which can be implanted within the main pulmonary artery in order to elevate flow resistance to palliate the patient's CHD symptoms and move toward systemic flow. The device includes a self-expanding metal frame or skeleton which constrains the device radially and axially attached to a balloon-expandable membrane, also referred to herein as a pulmonary artery resistor, that interacts with, the blood flow and provides flow constriction. The pulmonary artery resistor facilitates MIS intervention for modification of flow resistance.

The device may be deployed minimally invasively via catheter by a cardiac surgeon. As initially configured, the pulmonary artery resistor may provide the highest level of flow resistance possible. The highest level resistance would palliate patients with the most severe CHD symptoms, such as multiple and large septal tears the highest spectrum CHD cases. However, in those cases where less restriction is desired, the surgeon may use a balloon catheter of the desired size to incrementally expand the size of the resistor in situ. An adequate sized balloon is chosen and delivered over a guidewire to a location inside the resistor. The balloon is then dilated to expand the resistor. The balloon is then deflated and finally removed. This cycle ensures that the adjustment is performed quickly since a fully expanded balloon in the middle of the main pulmonary artery (Main PA) may cause an acute spike in pulmonary pressure and stress on the heart. Evaluation of the sufficiency of the resistance change provided by the pulmonary artery resistor is obtained after the dilation balloon has performed the expansion task and is fully removed from the patient, while the guidewire and femoral introducer catheter remain in place. A surgeon may incrementally alter the resistance further by stepping up the size of the balloon and repeating the dilation procedure. The expansion cycles continue until a satisfactory pulmonary arterial pressure is reached while adequate oxygenated blood flow to the aorta is also satisfactory.

Future follow on MIS procedures to reduce resistance may be periodically necessary to maintain desired apportionment of blood flow between the lungs and the remainder of the body as the patient grows. The minimally invasive procedure to correct the flow resistance should reduce or eliminate post-surgery recovery time in an intensive care unit and hospital stay duration when compared to conventional pulmonary artery banding which requires open surgery. The pulmonary artery resistor incorporates the flow constriction geometry necessary to create the desired flow without distorting the pulmonary artery wall.

In one embodiment, the frame of the resistor may be a tubular closed or open celled lattice made out of a shape memory alloy such as nitinol. The frame may be plated in gold or other radiopaque material or alloy to improve visibility inside the vessel. The frame may include eyelets with inserted radiopaque rivets that enhance visibility for the surgeon. In one embodiment the frame preferably includes at least two crossing arms, which preferably extend beyond its tubular radius. The arms may include slots for improved adhesion to the vasculature walls. The distal ends of the arms may feature tips that have an increased surface area and a backwards bend, essentially forming feet that reduce the contact pressure against the vessel wall. The arms may be tied together in the center to prevent the frame from collapsing under high pressure.

The resistor membrane may be a 2D annular shape or an annular shape stretched along the third axis forming a conical tube or funnel. The membrane may be made of an inelastic material that retains its new shape after deformation by the balloon as described above. The material may be woven or otherwise structured in such a way that the membrane preferentially stretches in the radial direction while minimizing foreshortening. The material may be an expanded polytetrafluoroethylene (ePTFE) or similar type material. The membrane may be attached to the frame chemically such as an adhesive bond, mechanically such as stitching, hook and loop, thermal bonding or related technology. The membrane may be extruded, wrapped, or otherwise formed separately from the frame and then attached in a post process. The membrane may also be formed directly on the frame via sputtering, wrapping, or other means. The expandable membrane may be attached on the proximal side of the device such that in the conical configuration the narrow end of the funnel extends distally down the center of the frame.

The resistor may be deployed through a transcatheter procedure by which the device is collapsed between an inner guidewire lumen and outer sheath lumen. In one embodiment, there may include two or more proximally located eyelets on the frame which may extend axially beyond the main body of the frame to interact with pins, hooks, recesses, or some other attachment mechanism attached to the guidewire lumen. When the frame is collapsed inside the catheter, with such an attachment mechanism engaged, the mechanism constrains the axial and rotational motion of the frame such that any motion of the attachment device translates into corresponding motion by the frame. This link may be used for ejection of the device out the distal end of the deployment catheter, for axially repositioning or rotating a semi-deployed device, or for re-sheathing a semi-deployed device.

FIG. 1 shows an example of a pulmonary artery flow resistor 10 including funnel shaped membrane 12 and self expanding frame 14. Membrane 12 has proximal base 16 having a wide opening 17 (e.g., with a diameter of between 10 and 18 mm) and a distal narrow opening or spout 18 (e.g., having a diameter of between 0.5 and 6 mm). Preferably, frame 14 is secured to the base 16 of the membrane. In one example, base 16 was 14 mm in diameter and restricted opening was 2 mm in diameter.

Figure 2:
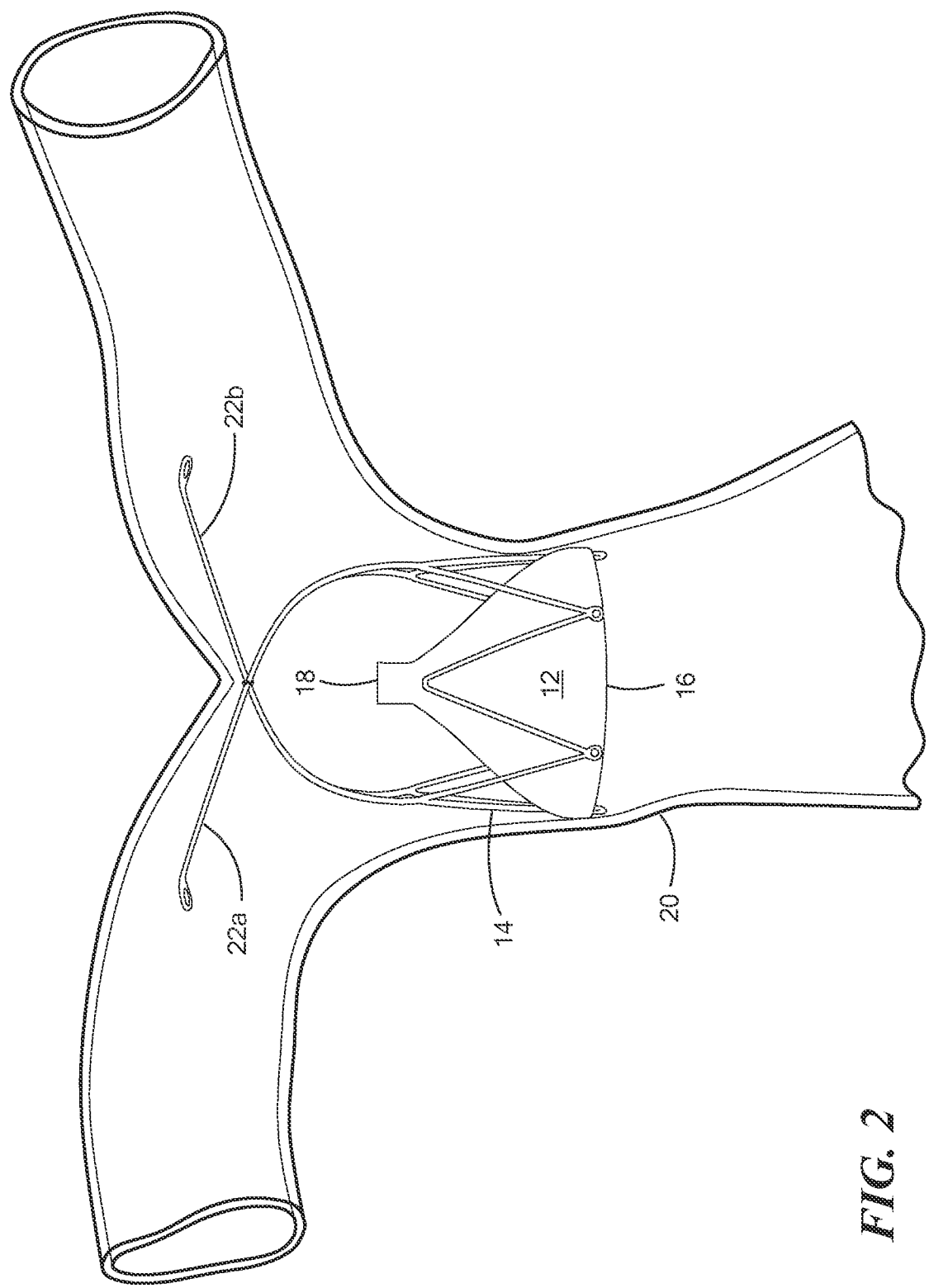
FIG. 2 is a schematic view showing the resistor of FIG. 1 deployed and in place within the pulmonary artery.

The membrane functions to resist blood flow through the pulmonary artery 20, FIG. 2 since, when the flow resistor is in place in the pulmonary artery 20, blood is restricted to only flow out distal narrow opening 18 of membrane 12 since base 16 is urged against the inner wall of the artery. Frame 14 functions to retain membrane 12 in place in the pulmonary artery. Also, using a balloon catheter, the distal narrow opening 18 of membrane 12 can be enlarged in diameter by placing a balloon catheter inside opening 18 and expanding the balloon catheter whereupon the material of the membrane in the area of opening 18 stretches via the balloon catheter and retains its new, now larger diameter. Thus, preferably, membrane 12 is made of polytetrafluoroethylene (ePTFE) or similar type polymer material typically between 0.3 thousandths of an inch and 3 thousandths of an inch thick. Other polymers may be used.

Frame 14 may be made of a shape memory alloy such as Nitinol. Frame 14 may further include inwardly bent arms 22a and 22b extending upward over membrane 12 and crossing above restricted opening 18 as shown in FIGS. 1 and 2. The arms may each extend into a branch of the pulmonary artery as shown. The arms 22a, 22b have a large surface area to reduce pressure on the pulmonary artery wall and function to anchor membrane 12 in place against the normal blood flow.

As shown in FIGS. 1-2, frame 14 is a stent like in structure and being self expanding it expands the membrane 12 and maintains contact with pulmonary artery wall even as the pulmonary artery grows in size.

Preferably, frame 14 includes circumferential lower spaced apexes 30a, 30b, 30c and the like and upper spaced apexes 32a, 32b, 32c, and the like each between adjacent lower apexes. The lower apexes may be secured to the proximal base 16 of membrane 12. Arms 22a, 22b may include members extending from select upper apexes of the frame. So, for example, arm 22b includes member 34a extending from apex 32a and member 34b extending from adjacent apex 32b. Crossing arms 22a, 22b may be include downwardly bent distal eyelet tips 36a, 36b, respectively. Furthermore, lower apexes 30a, 30b, 30c, and the like may include eyelets 38a, 38b, and 38c, and the like, respectively. Eyelet 38a and the eyelet directly across from it may be slightly enlarged and constitute deployment eyelets which fit over deployment pins associated with a deployment device. The other eyelets (e.g., 38b, 38c, and the like) may be used to secure the frame 14 to be base of member 12. The entire frame including the arms may be formed by cutting a single thin tube of Nitinol which is then expanded on a mandrel and then heat treated so that it naturally retains this expanded shape. Radiopaque stripes 15a, 15b may be included (printed on or adhered to) on membrane 12 to enable visualization of the membrane during deployment into the pulmonary artery. Frame 14 may include a radiopaque coating to enable visualization of the frame during deployment into the pulmonary artery. In some examples, the flow resistor reduces the effective diameter of the pulmonary artery to 2 mm, a diameter which can be changed by using a balloon catheter to expand the flow resistor. The flow resistor may provide a maximum pressure drop of 40-50 mm Hg in the pulmonary artery and resist the blood flow rate to a maximum of 1.5-2 L/min. If the membrane is fully expanded, the flow resistor would produce no pressure drop and no flow rate reduction. In testing, the flow restrictor shown in FIG. 1 could be collapsed down into a 2 mm diameter package and then expanded such that base 16 and frame 14 were 13 mm-14 mm in diameter (or equal to the vessel diameter). The height of the membrane may be 8-16 mm. The frame may be 5-15 mm (from upper apex to lower apex) and the arms may be 15-30 mm long.

Figure 3:
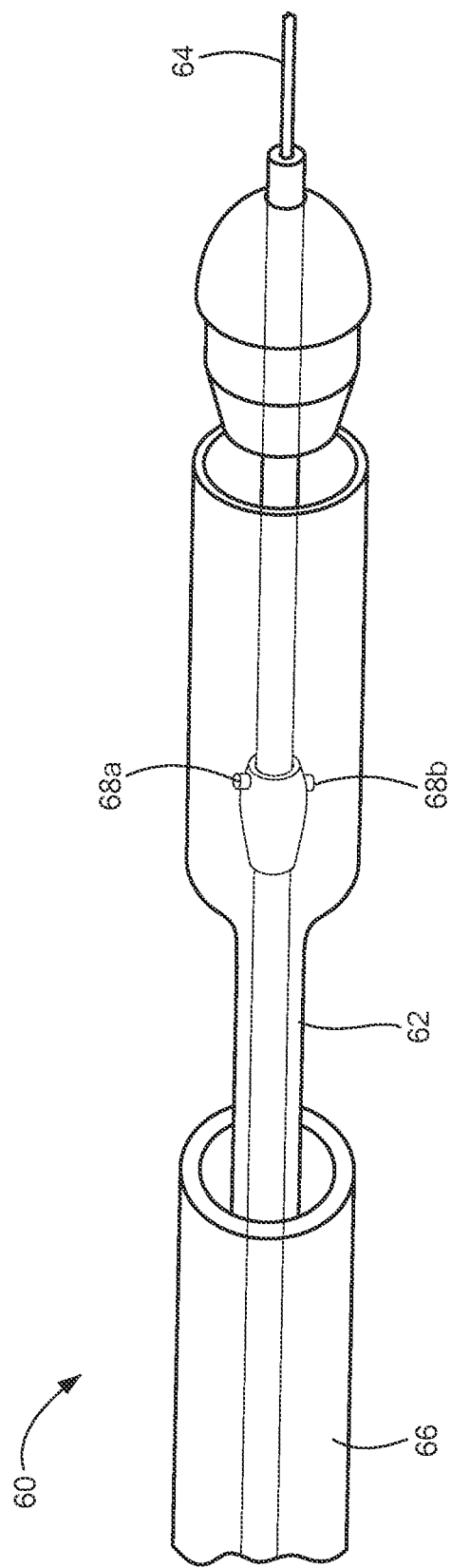
FIG. 3 is a schematic view of a transcatheter device for delivery a pulmonary resistor into the pulmonary artery.

The system may further include transcatheter device 60, FIG. 3 for delivering the membrane and the frame into the pulmonary artery. The delivery device preferably includes inner braided guide wire lumen about guide wire 65 and retractile lumen 66 (e.g., 3-5 Fr) which is retractable relative to inner lumen 62 and flared at its tip (to, e.g., 5-9 Fr) forming a garage section. The frame is releasably attached to the inner lumen, for example, by placing opposing deployment eyelets on pins 68a, 68b. Thus the frame and the membrane are collapsed and reside between lumen 66 and lumen 62. An outer support sheath 70 may also be provided. Braided guide wire lumen 62 may be thinned out just before a garage section giving maximum space between the garage section and guide wire lumen 62 in order to fit the restrictor device. The tip of the transcatheter device and the deployment pins 68a, 68b are attached to the thinned portion of guide wire lumen 62. The outer most lumen 70 serves to reduce friction for the retractile lumen 66 as it retracts relative to outer lumen 70. Outer lumen 70 terminates before the garage section giving space for the translation. The retractile sheath 66 slides along the lubricious outer lumen inner liner rather than along the vessel walls.

Figure 4A:
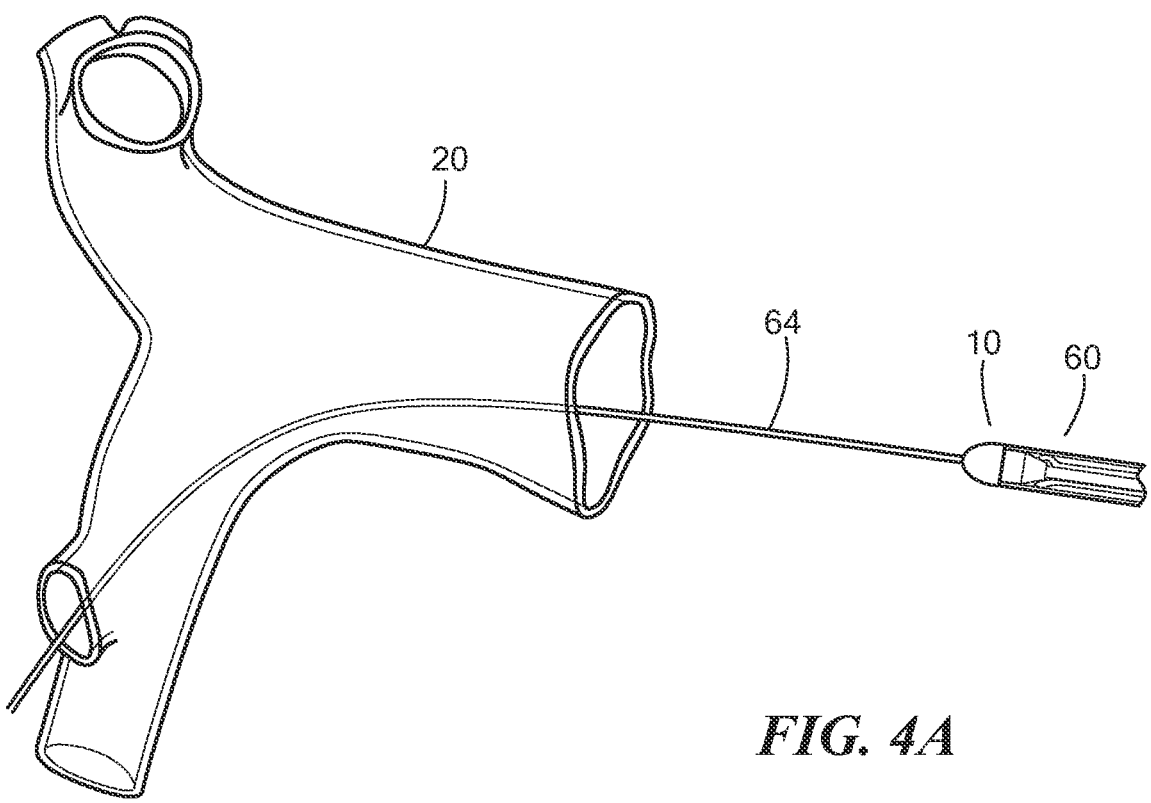
FIGS. 4A 4H are schematic views showing the delivery of the pulmonary artery flow resistor into the pulmonary artery.
Figure 4B:
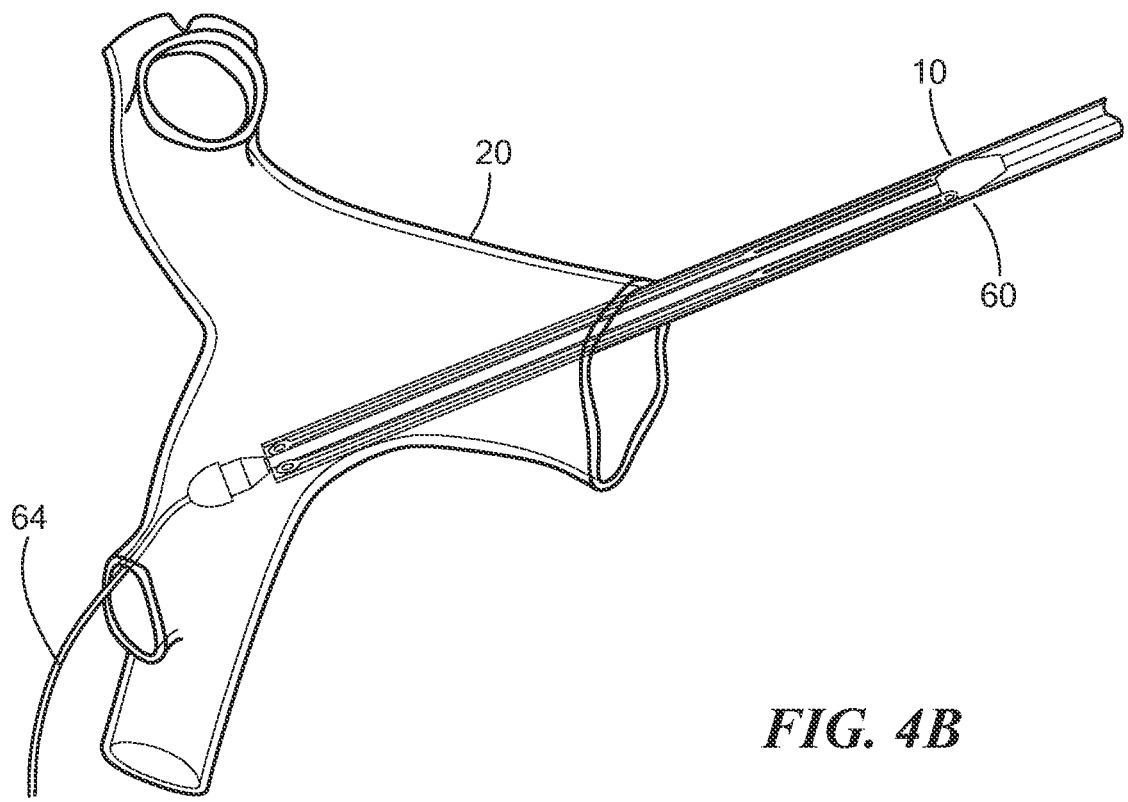
Figure 4C:
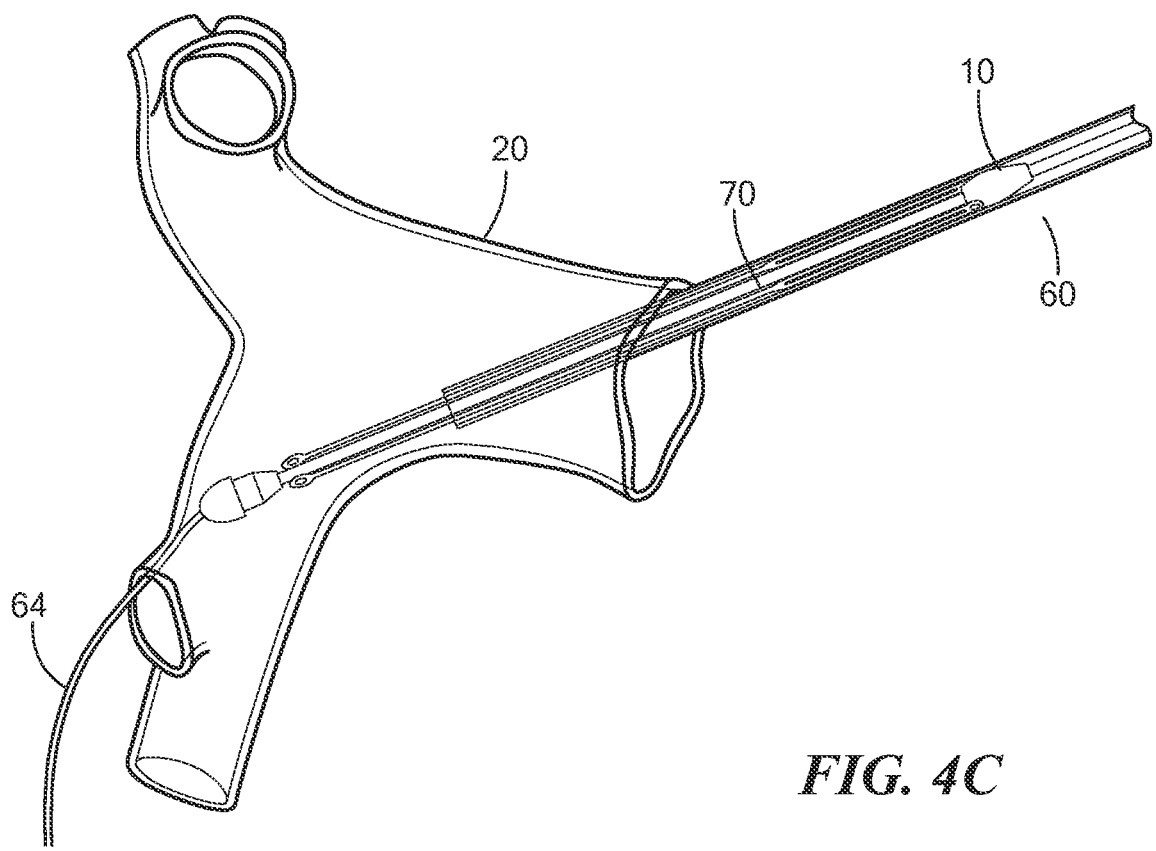
Figure 4D:
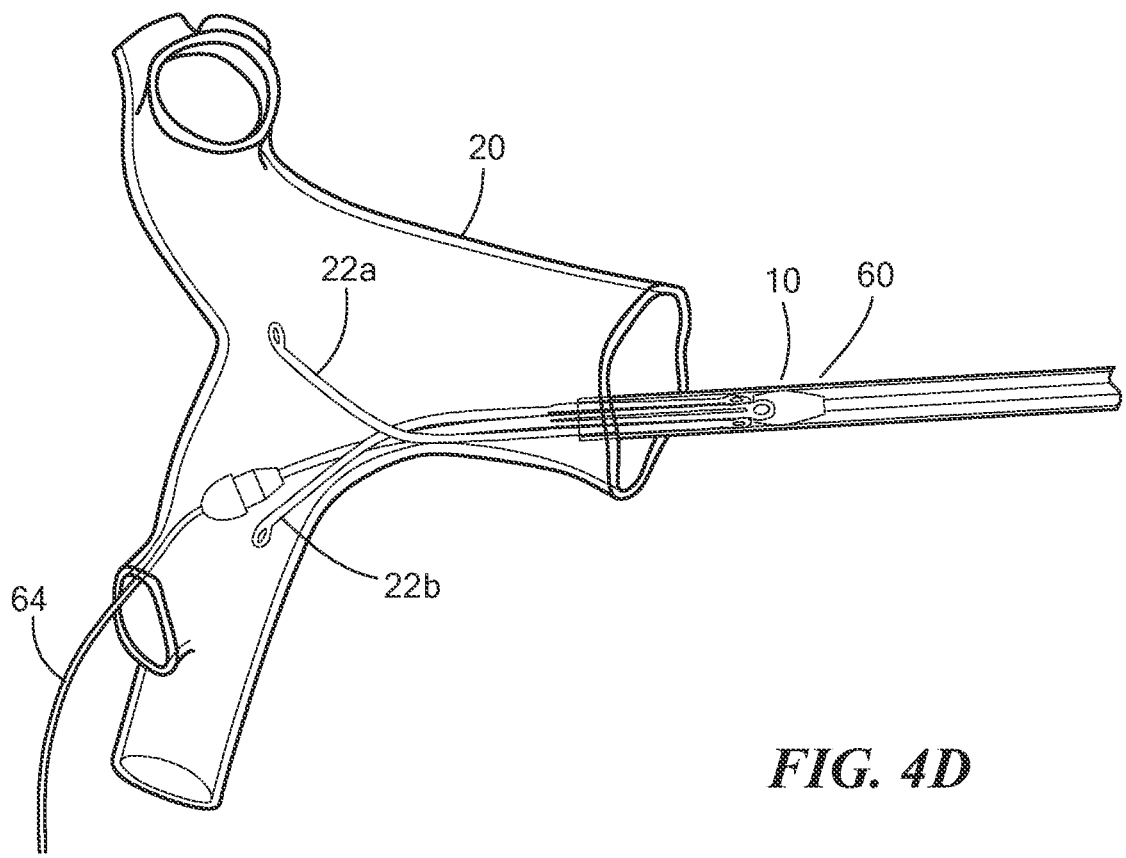
Figure 4E:
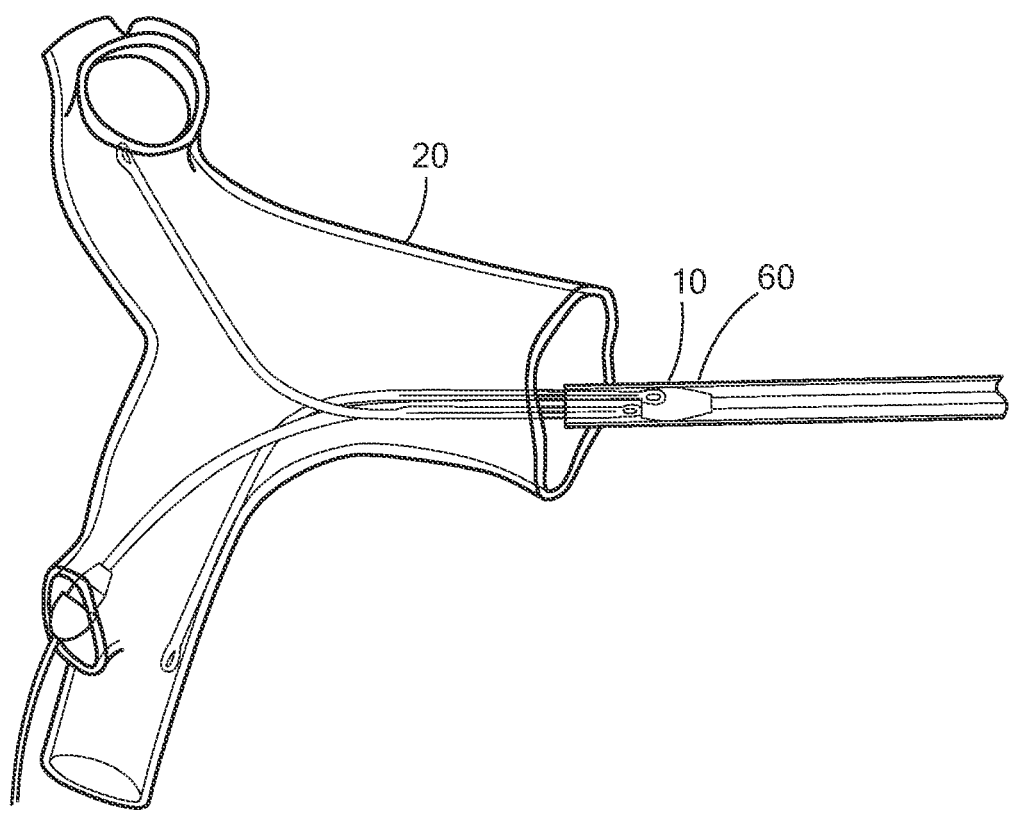
Figure 4F:
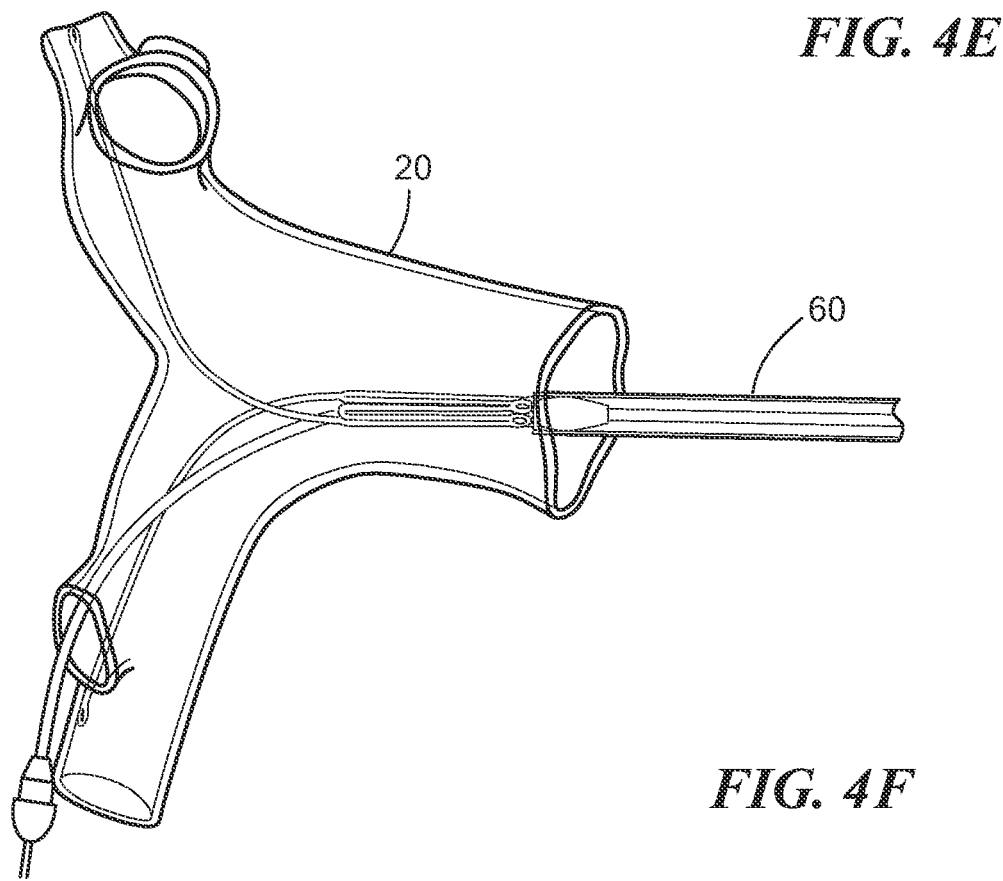
Figure 4G:
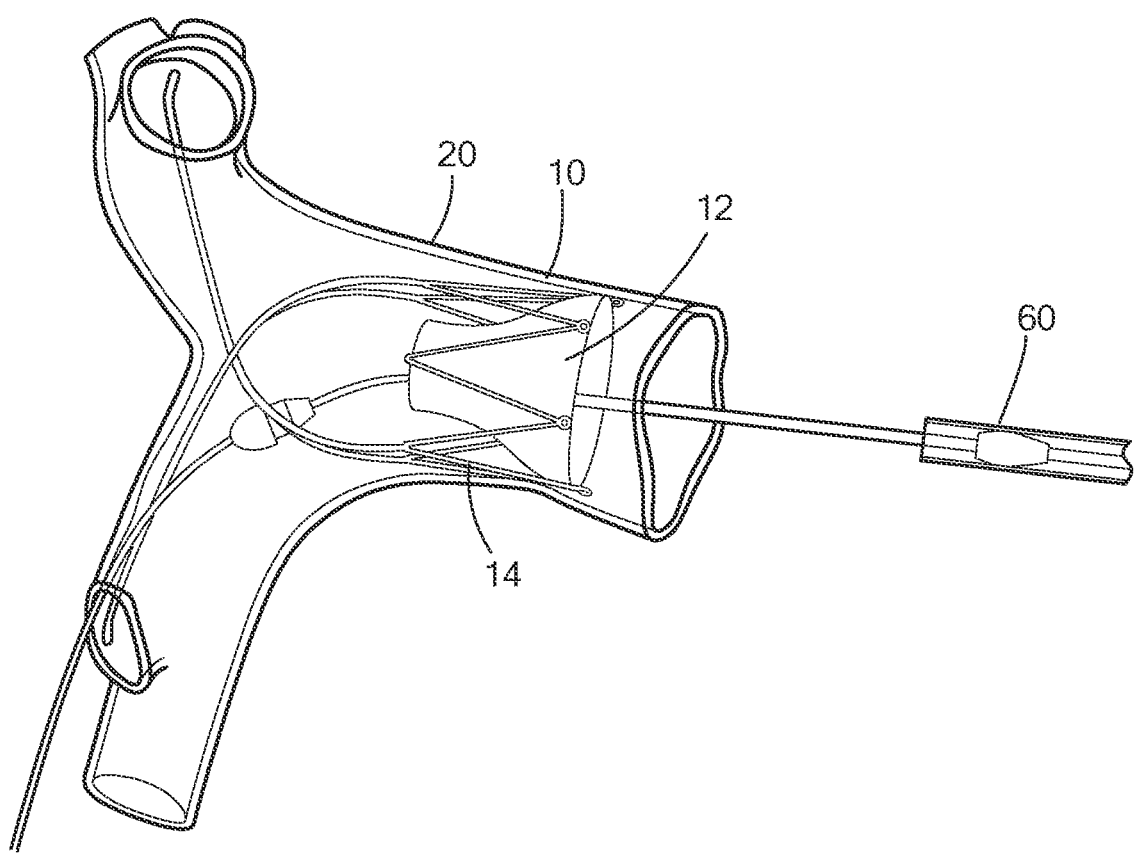
Figure 4H:
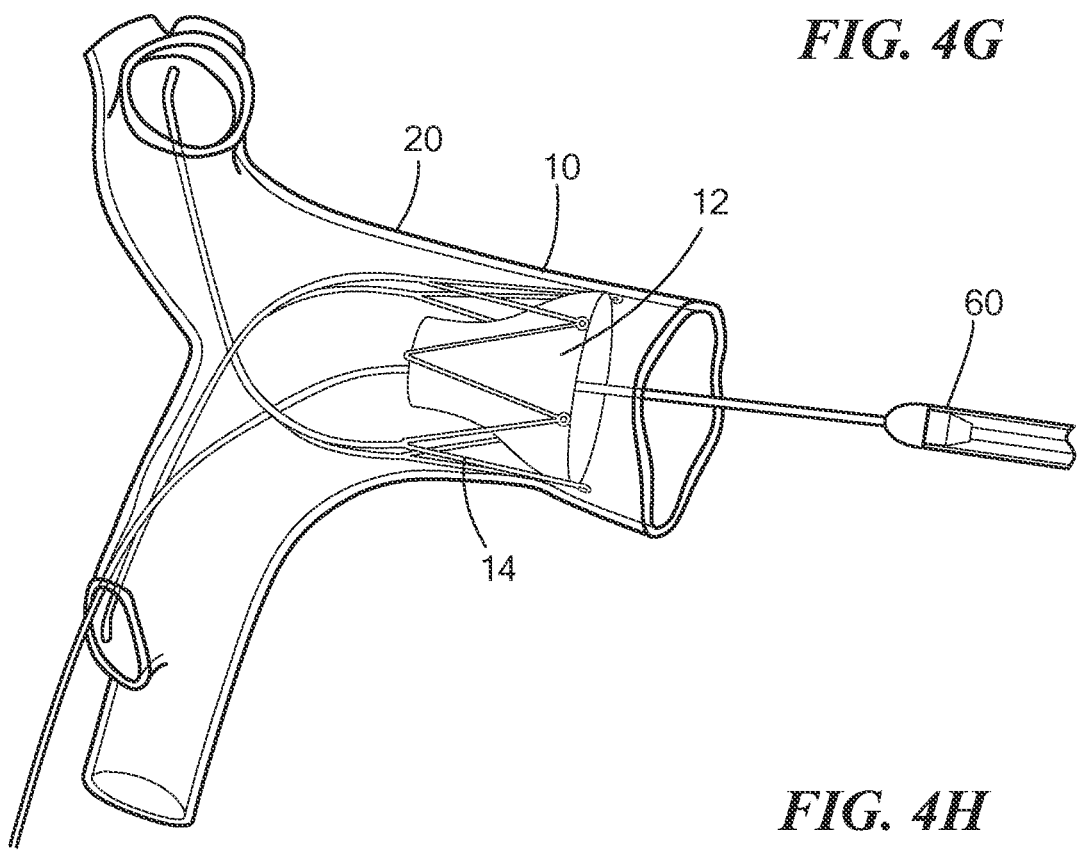

FIG. 4A shows catheter 60 following the guide wire 20 to the artery. In FIG. 4B the catheter continues past the valve to just beyond the split in the pulmonary artery. In FIG. 4C the lumen 66 is pulled back to reveal the arms of the restrictor frame. In FIG. 4D the hymen 66 is pulled hack more until the arms begin to separate and in FIG. 4E the catheter is gradually pushed forward keeping the outer sheath hack. The inner lumen 62 is then advanced, FIG. 4F until the deployment pins reach the end of the sheath and in FIG. 4G the lumen 66 is pulled back allowing the frame and the membrane to spring into position. In FIG. 4H, the catheter and the guide wire are removed leaving the flow restrictor in place.

Figure 5:
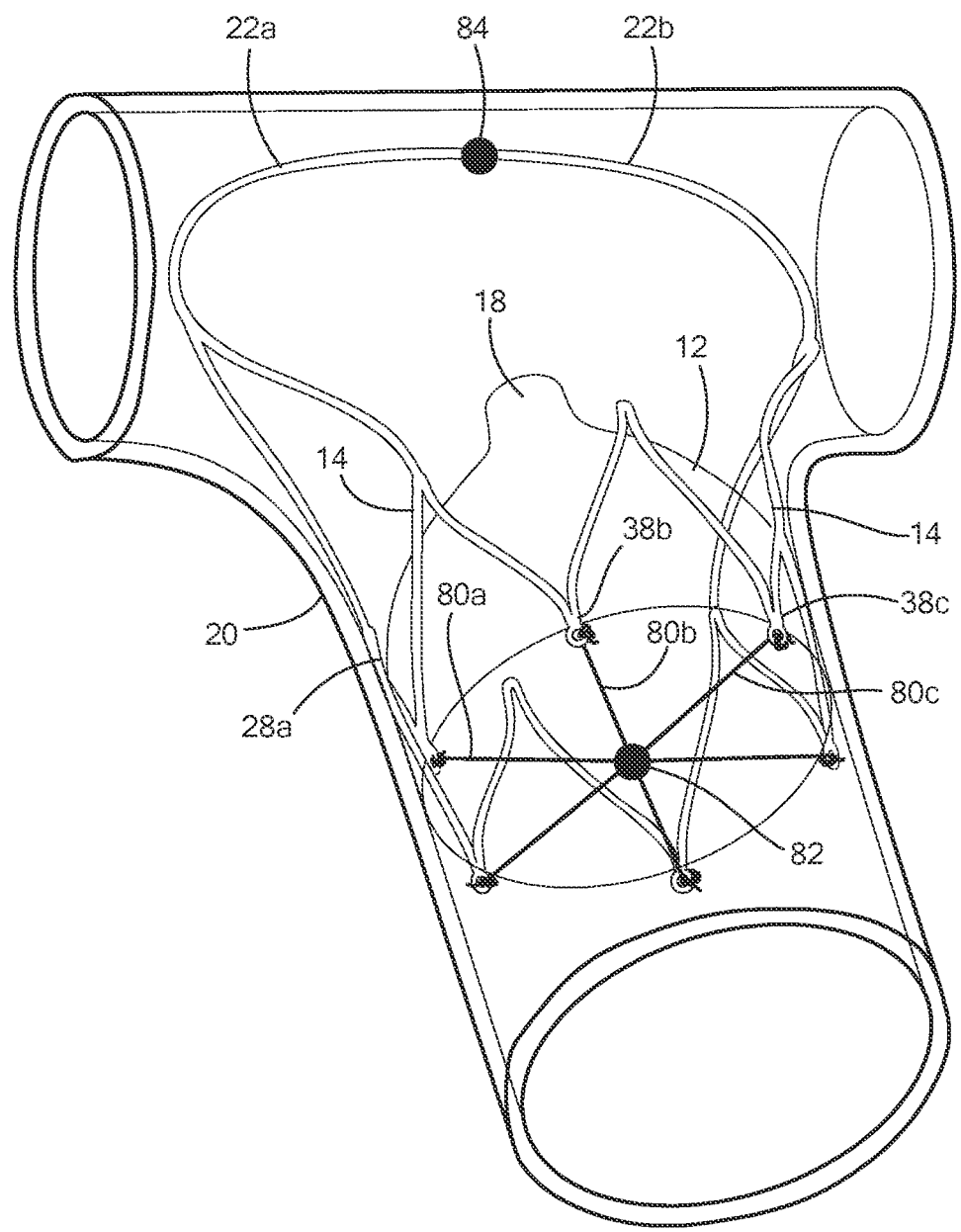
FIG. 5 is a schematic view showing another example of a pulmonary artery flow resistor.

FIG. 5 shows a design where one or more flexible lines (e.g., sutures) 80 are connected to frame 14 for collapsing the frame and removing the frame and the membrane 12 from the pulmonary artery 20. As shown in the example of FIG. 5 a suture 80a, 80b, 80c are each secured to the lower apexes 38a, 38b, 38c, respectively of frame 14 to form a web with a hook, loop, hall, knot, or other feature 82 tying the other end of all the sutures together in the center. This feature 82 may be snared by a standard transcatheter snare. Also in this embodiment, arms 22a, 22b may be flared members in a light bulb shape as shown with two or three arms intersecting in the center where they are sutured together as shown as 84. The suture keeps the arms in place and acts as a hinge allowing the arms to collapse into the outer lumen during deployment or during retrieval. The light bulb shape of the arms fit into the T of the artery. A snare may be guided through an outer lumen to grab onto feature 82 and then pulled hack into the outer lumen whereupon frame 14 collapses by the force on sutures 80.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A pulmonary artery flow restrictor system comprising:
    a funnel-shaped membrane for installation in an artery and including:
        a wide area base opening to receive arterial blood flow, and
        a distal narrower area spout to restrict the arterial blood flow therethrough to a predetermined blood flow rate; and
    a self-expanding stent structure associated with the membrane to support the membrane in the artery and spaced arms extending upwardly and over the funnel-shaped membrane distal narrower area spout.

2. The system of claim 1 in which the funnel-shaped membrane is made of an inelastic material so that if the distal narrower area spout is expanded it retains its expanded shape.

3. The system of claim 1 in which the wide area base opening is about 10-18 mm in diameter and the distal narrower area spout is about 0.5-6 mm in diameter.

4. The system of claim 1 in which the spaced arms are integral with the self-expanding stent structure.

5. The system of claim 1 in which the funnel shaped membrane is made of a polymer.

6. The system of claim 5 in which said polymer is polytetrafluoroethylene (ePTFE).

7. The system of claim 1 in which the self expanding stent structure is made of a shape memory alloy.

8. The system of claim 7 in which said shape memory alloy is Nitinol.

9. The system of claim 1 in which the self expanding stent structure includes a wire bent to form a series of spaced lower apexes and a series of spaced upper apexes.

10. The system of claim 9 in which the spaced lower apexes are secured to the base of the funnel shaped membrane.

11. The system of claim 1 further including one or more flexible lines connected to the self expanding stent structure for collapsing the self expanding stent structure.

12. The system of claim 1 further including a transcatheter device for delivering the membrane and self expanding stent structure into the pulmonary artery.

13. The system of claim 12 in which the transcatheter device includes an inner lumen about a guide wire and a retractable lumen retractable relative to the inner lumen.

14. The system of claim 13 in which the self expanding stent structure is removably attached to the inner lumen.

15. The system of claim 14 in which there are pins attached to the inner lumen and the self expanding stent structure includes eyelets receiving said pins therethrough.

16. The system of claim 1 in which the predetermined blood flow rate is 1.5-2 L/min.

* * * * *